United States Patent [19]

Horiuchi et al.

[11] Patent Number: 4,486,334

[45] Date of Patent: Dec. 4, 1984

[54] METHOD FOR THE PREPARATION OF AN AQUEOUS DISPERSION OF PEARLESCENT AGENT

[75] Inventors: Teruo Horiuchi, Sayama; Nobuo Jona, Funabashi; Kazuo Ohbu, Yokohama; Naoki Mizushima, Ichikawa, all of Japan

[73] Assignee: Lion Corporation, Tokyo, Japan

[21] Appl. No.: 362,535

[22] Filed: Mar. 26, 1982

[30] Foreign Application Priority Data

Apr. 3, 1981 [JP] Japan .................................. 56-50296

[51] Int. Cl.³ .......................... B01J 13/00; C09K 3/34
[52] U.S. Cl. ............................ 252/312; 252/DIG. 13;
    252/DIG. 14; 252/354; 252/356; 252/542;
    252/544; 252/299.01; 252/299.5; 252/299.6;
    252/314
[58] Field of Search ............... 252/312, 354, 355, 357,
    252/542, 546, 545, 547, DIG. 13, DIG. 14,
    299.01, 299.5, 299.6

[56] References Cited

U.S. PATENT DOCUMENTS

| 4,007,261 | 2/1977 | Sorrentino et al. | 424/70 |
| 4,234,437 | 11/1980 | Friberg et al. | 252/62.51 |
| 4,243,549 | 1/1981 | Messenger et al. | 252/355 |
| 4,363,755 | 12/1982 | Uchino et al. | 252/545 |

FOREIGN PATENT DOCUMENTS

| 45-36589 | 11/1970 | Japan . |
| 48-17528 | 5/1973 | Japan . |
| 55-23156 | 2/1980 | Japan . |
| 2023637 | 1/1980 | United Kingdom . |
| 2031455 | 4/1980 | United Kingdom . |

OTHER PUBLICATIONS

Gray & Winsor, *Liquid Crystals & Plastic Crystals*, vol. 2, John Wiley & Sons, N.Y., p. 53, (1976).

*Primary Examiner*—Richard D. Lovering
*Assistant Examiner*—Anne Brookes
*Attorney, Agent, or Firm*—Brisebois & Kruger

[57] ABSTRACT

The invention provides a novel and improved method for the preparation of a highly concentrated aqueous dispersion of a pearlescent agent, which is typically an ethyleneglycol di(fatty acid) ester, capable of forming very thin leaf crystals exhibiting pearlescence to be used for imparting pleasant appearance to detergents, toiletries, such as hair shampoos, hair rinses and others, and the like admixed therewith. The method is performed by solubilizing the pearlescent agent in an aqueous solution of a surfactant, at least a substantial amount thereof being in the state of middle phase liquid crystals, at or above the melting point of the pearlescent agent and succeedingly cooling the above obtained mixture to room temperature whereby to crystallize the pearlescent agent in situ while the state of the middle phase liquid crystals of the surfactant is kept substantially unchanged.

9 Claims, No Drawings

METHOD FOR THE PREPARATION OF AN AQUEOUS DISPERSION OF PEARLESCENT AGENT

BACKGROUND OF THE INVENTION

The present invention relates to a novel method for the preparation of a highly concentrated aqueous dispersion of a pearlescent agent used for imparting pearlescence to liquid detergents and toiletries.

It is a common practice that detergents and toiletries, such as shampoos, hair rinses, lotions, creams, soaps and the like, are imparted with pearlescence in order to improve their attractiveness and to enhance their value as commercial products. Hitherto known pearlescent agents used to impart such pearlescence are thin leaf materials of natural origin such as fish scale and mica, of which fish scale is particularly preferred.

Fish scale however, presents several problems. In addition to the low availability of high quality materials and the corresponding high cost, fish scale contains impurities which cause deterioration of and on unpleasant odor in the products formulated therewith. Therefore, fish scale is not a wholly satisfactory material for the pearlescent agent. Accordingly, as a recent trend in the industries of detergents and toiletries, fish scale is being replaced with fatty acid esters of glycols which are more readily available and capable of exhibiting pearlescence almost as good as that obtained with the pearlescent agents made from fish scale.

In order to exhibit good pearlescence, the material contained in the aqueous dispersion should be composed of very thin leafy crystals having a large light reflecting surface. With an object to control the crystal growth suitably, accordingly, crystallization of the pearlescent agent in the final product is usually carried out by precise adjustment of the formulation of the composition and the cooling velocity thereof.

Such a method of crystallization of the pearlescent agent, by in situ crystallization in the final product, has, however, limitations in the control of the crystallization conditions leading to difficulty in improving the pearlescence. Present research is, therefore, directed to the development of a new material for the pearlescent agent rather than to the improvement of the crytallization method. An alternative way has been proposed, as is disclosed in Japanese Patent Publication No. 47-804, which attempts to prepare a highly concentrated aqueous dispersion of the pearlescent agent. If an aqueous dispersion of a pearlescent agent in a concentrated form is used, manufacturing processes of many toiletry products can substantially be simplified with a possiblity of reducing the production costs.

The inventors have extensively investigated preparation of a highly concentrated aqueous dispersion of a pearlescent agent comprising a fatty acid diethanolamide and have attained a certain degree of success. The above proposed method has, however, a disadvantage of limited applications because of the necessity of a relatively large amount of the fatty acid diethanolamide.

Accordingly, there has been a strong desire to develop a novel and improved method for the preparation of a pearlescent agent, in particular, a highly concentrated aqueous dispersion thereof free from the above described problems and disadvantages of the prior art methods.

SUMMARY OF THE INVENTION

An object of the present invention is therefore to provide a novel and improved method for the preparation of a highly concentrated aqueous dispersion of a pearlescent agent free from the disadvantages of the prior art methods. The invention is based on the discovery that very thin leafy crystals of a pearlescent agent are readily obtained when a molten pearlescent agent is solubilized into a concentrated solution of a surfactant, in which the surfactant forms the middle phase i.e. $M_1$ phase of liquid crystal, and is then precipitated by cooling.

The method of the present invention, according to which a highly concentrated aqueous dispersion of a pearlescent agent is readily obtained by the aid of two essential steps, comprises solubilizing a pearlescent agent in an aqueous solution of a surfactant, at least about a half amount or at least a substantial amount thereof forming the middle phase liquid crystal, at a temperature higher than the melting point of the pearlescent agent and then cooling the mixture to crystallize the pearlescent agent while the surfactant is kept in the state of the middle phase liquid crystal.

In particular, the temperature at which the pearlescent agent is solubilized is preferably in the range from 50 to 95° C. and the amount of the pearlescent agent is preferably in the range from 3 to 45% by weight based on the amount of the resultant aqueous mixture, i.e. the total amount of the pearlescent agent and the aqueous solution of the surfactant.

DETAILED DESCRIPTION OF THE PREFERRED EMBODIMENTS

In carrying out the crystallization of the pearlescent agent in the aqueous solution of a surfactant according to the inventive method, it is necessary that the condition of molecular association of the surfactant should be kept substantially unchanged and at least about a half amount of the surfactant should form the middle phase liquid crystal throughout the process of crystallization, the balance being maintained as deformed spherical, e.g. spheroidal, micelles when the concentration is relatively low, or as lamellar phase liquid crystals. For the purpose of discussion below, the term "micelle" is taken to mean any thermodynamically stable association units of the surfactant molecules. The pearlescent crystals formed from the deformed spherical micelles have relatively small size so that they are less preferred to those formed from the middle phase liquid crystals. Further, the pearlescence of the crystals formed from the lamellar micelles is also somewhat inferior to those formed from the middle phase liquid crystals since the crystal size distribution may not be uniform even though large crystals can be obtained. Therefore, in order to obtain very thin leafy crystals exhibiting excellent pearlescence, it is desirable that the number of crystals formed from the deformed spherical micelles and lamellar micelles should be as small as possible.

The method of the invention comprises confining the molecules of the solubilized pearlescent agent within the hydrophobic regions of the micelles followed by in situ crystallization by cooling so that the association state of the micelles is kept substantially unchanged throughout the whole course of the crystallization. Furthermore, the pearlescent agent itself should preferably take a liquid crystal structure when solubilized in the middle phase liquid crystals and thin leafy crystals are formed therein readily by cooling.

The surfactant used in the invention is not particularly limited to a specific one but may be any one of known substances which can form the middle phase including anionic, cationic, amphoteric and nonionic surfactants. They may be used either individually or as a combination of two kinds or more. Those surfactants incapable of forming the middle phase, such as the fatty acid diethanolamides, are not suitable. Even when such a surfactant is used as combined with one or more of other surfactants, the amount thereof should be limited in such a range that the formation of the middle phase can be ensured.

The surfactant satisfactorily to be used in the inventive method should be selected from those capable of forming the middle phase with sufficient stability in a wide range of the concentration to prevent the transfer of the pearlescent agent from the elongated cylindrical micelles into the aqueous medium. Exemplary of useful surfactants are: anionic surfactants such as long-chain alkylbenzene sulfonates, alkylether sulfates, alkyl sulfates, α-olefin sulfonates, salts of fatty acids, N-acyl glutamates, N-acyl taurides, O-alkylhydroxyalkane sulfonates and the like; cationic surfactants such as monoalkyl-type quaternary ammonium salts, e.g. long-chain alkyl trimethyl ammonium salts and long-chain alkyl dimethyl benzyl ammonium salts, alkyl pyridinium salts, alkyl imidazolinium salts and the like; amphoteric surfactants such as long-chain alkyl dimethyl carboxymethyl ammonium betaines, alkyl carboxymethyl imidazolinium betaines, N-(N'-acylaminoalkyl)-N-hydroxyalkyl aminocarboxylates and the like; and nonionic surfactants having an HLB value of about 13 or larger such as polyoxyethylene nonyl phenyl ethers where the number of moles of ethyleneoxide addition (referred to as $\bar{P}$ hereinafter) in the range from about 9 to about 100, polyoxyethylene octyl phenyl ethers having a $\bar{P}$ of from about 8 to about 100, polyoxyethylene dodecyl phenyl ethers having a $\bar{P}$ of from about 11 to about 100, polyoxyethylene lauryl ethers having a $\bar{P}$ of from about 7 to about 100, polyoxyethylene ethers with $C_{11}$–$C_{15}$ oxoalcohols having a $\bar{P}$ of from about 7 to about 100, polyoxyethylene distearic acid esters having a $\bar{P}$ of from about 100 to about 250 and the like.

The concentration of the surfactant in the aqueous solution containing the pearlescent agent should be such that at least a substantial amount or at least half of the surfactant can form the middle phase liquid crystals throughout the temperature range covering the melting point of the pearlescent agent and the temperature at which the crystallization thereof begins. In particular, the concentration of the surfactant should be maintained in such a range where the middle phase liquid crystals are the main part of the micelles in the temperature range from 50 to 95° C. The formation of the middle phase liquid crystals can readily be detected by the observation with a polarizing microscope or by the measurement of the half-width in the NMR spectrum.

In the binary system composed of water and a surfactant, substantially all of, for example, a sodium α-olefin sulfonate having a $C_{14}$ hydrophobic chain is in the form of the middle phase liquid crystals when the concentration thereof is in the range from 40 to 58% by weight. Therefore, the preferable range of the surfactant concentration is from 35 to 65% by weight for the inventive method. The preferable range of the concentration basically depends on the kind of the surfactant and, for example, the range is from about 30% to about 50% by weight and from about 40% to about 75% by weight for a sodium polyoxyethylene lauryl ether sulfate with a $\bar{P}$ of 3 and a longchain alkyl quaternary ammonium chloride, respectively.

On the other hand, the concentration of the pearlescent agent in the aqueous solution of the surfactant is determined by the limitation within which the pearlescent agent can be solubilized into the micelles of the surfactant in the aqueous solution. Generally speaking, satisfactory solubilization of the pearlescent agent can be obtained when the amount of the pearlescent agent is in the range from 3 to 45% by weight based on the amount of the resultant aqueous mixture, i.e. the total amount of the pearlescent agent and the aqueous solution of the surfactant. The upper limit of the amount of the solubilizable pearlescent agent basically depends on the type of the surfactant. For example, the upper limits of the pearlescent agent is 80, 50 and 60 parts by weight for the anionic, cationic and amphoteric surfactants, respectively, per 100 parts by weight of the aqueous solution of the respective surfactant, the lower limit of 3 parts by weight being approximately the same for each type of the surfactants.

The pearlescent agent used in the inventive method is an organic compound having a melting point of 50 to 80° C. and capable of forming thin leafy crystals. In particular, those compounds capable of being solubilized by taking a liquid crystal structure in the cylindrical micelles of the middle phase liquid crystals of the surfactant are preferred. Suitable pearlescent agents are, for example: ethyleneglycol dipalmitate, ethyleneglycol distearate, diethyleneglycol dipalmitate, diethyleneglycol distearate, 1,3-propanediol dipalmitate, 1,3-propanediol distearate, 1,4-butanediol dipalmitate, 1,4-butanediol distearate, 1,4-butanediol diarachidate, dipalmityl succinate, distearyl succinate, dipalmityl adipate, distearyl adipate and the like. They are used either singly or as a comination of two kinds or more.

In the inventive method, the cooling rate of the aqueous mixture has almost no influences on the result of the method since the crystallization of the pearlescent agent solubilized in the cylindrical micelles of the middle phase liquid crystals takes place in situ as the temperature of the aqueous mixture decreases. Accordingly, cooling of the aqueous mixture can be performed by any conventional procedures including rapid cooling, compulsory cooling with programmed temperature control and cooling by merely keeping under ambient condition. From the standpoint of the operational efficiency, of course, compulsory cooling is preferred by use of any cooling equipments more or less.

In the aqueous dispersion of the pearlescent agent prepared according to the invention, the ratio of the number of the thin leafy pearlescent crystals to the number of the cylindrical micelles is approximately 1:1 and the solubilized pearlescent agent forms a liquid crystal structure so that the thickness of the crystals formed there is extremely small to exhibit unexpectedly excellent pearlescence. Further, the fluidity of the highly concentrated aqueous dispersion of the pearlescent agent obtained according to the inventive method is relatively low even at room temperature owing to the relatively high concentration of the surfactant in the aqueous phase. Therefore, according to need, the aqueous dispersion can optionally be diluted with a suitable solvent or solvent mixture of water, water and alcohol, water and a glycol and the like until a desired concentration or consistency is obtained.

The aqueous dispersion of a pearlescent agent prepared according to the inventive method can be used in almost all kinds of formulations such as shampoos, hair rinses, lotions, creams, soaps and the like which may contain a surfactant with an object to improve their quality as a commercial product. The aqueous dispersions of a pearlescent agent prepared by the conventional crystallization process inevitably contain an anionic surfactant and are not applicable to a cationic surfactant-based formulation such as hair rinses or, at least, the application thereof is limited to some extent due to the existence of a fatty acid diethanolamide. According to the invention, in contrast, aqueous dispersions of the pearlescent agent can readily be prepared with a cationic surfactant and a great advantage is obtained that any detergent and toiletry formulations can be imparted with excellent pearlescence since the type of the surfactant is not limitative and can be selected according to the requirement.

In the following, the method of the present invention is described in further detail by way of examples.

In the following examples, the pearlescence of each of the preparations was graded by visual examination of the appearance into four classes of 5, 4, 3 and 2 corresponding to "excellent", "good", "fair" and "poor" pearlescence, respectively. The observation of the appearance was undertaken with uniformly diluted samples each containing 3% by weight of the pearlescent agent and a necessary amount of a 17% by weight aqueous solution of a sodium polyoxyethylene lauryl ether sulfate.

EXAMPLE 1

A uniform aqueous mixture was prepared by heating at 80° C. a mixture composed of 60 parts by weight of a 50% by weight aqueous solution of a sodium α-olefinsulfonate with the number of carbon atoms of 14 and 40 parts by weight of an ethyleneglycol di(fatty acid) ester (referred to as PSE hereinafter) containing about 6% by weight of the unreacted fatty acids and about 6% by weight of the monoesters with the weight ratio of palmitic acid/stearic acid of 4/6 as the pearlescent agent. After confirmation of the formation of the middle phase liquid crystals in this mixture, the mixture was gradually cooled with agitation down to room temperature whereby thin leafy crystals were formed in the mixture to give a highly concentrated aqueous dispersion of the pearlescent agent.

This aqueous dispersion exhibited excellent pearlescence and was evaluated as grade 5 in the appearance.

EXAMPLE 2

A highly concentrated aqueous dispersion of the pearlescent agent was prepared in the same manner as in Example 1 except that the sodium α-olefinsulfonate in Example 1 was replaced with a sodium polyoxyethylene ($\bar{P}=3$) lauryl ether sulfate.

Since the aqueous dispersion of the pearlescent agent thus obtained did not show sufficient fluidity, it was diluted with water into a 20% by weight dispersion. The aqueous dispersion exhibited excellent pearlescence and was evaluated as grade 5 in the appearance.

EXAMPLE 3

A uniform aqueous mixture composed of 30 parts by weight of the PSE as the pearlescent agent, 30 parts by weight of a mixed $C_{16}$–$C_{18}$ monoalkyl trimethyl ammonium chloride and 40 parts by weight of water was prepared by heating at 80° C. After confirmation of the formation of the middle phase liquid crystals in the aqueous mixture, it was gradually cooled down to room temperature to form thin leaf crystals.

The aqueous dispersion of the pearlescent agent thus obtained exhibited excellent pearlescence and was evaluated as grade 5 in the appearance.

EXAMPLE 4

An aqueous dispersion of the pearlescent agent was prepared in the same manner as in Example 3 except that the quaternary ammonium salt in Example 3 was replaced with lauryl dimethyl carboxymethyl ammonium betaine.

The aqueous dispersion of the pearlescent agent thus obtained exhibited excellent pearlescence and was evaluated as grade 5 in the appearance.

EXAMPLE 5

A uniform mixture composed of 20 parts by weight of the PSE as the pearlescent agent, 50 parts by weight of a polyoxyethylene di(stearic acid) ester having an average molecular weight of about 9000 and 30 parts by weight of water was prepared by heating at 80° C.

The aqueous dispersion of the pearlescent agent thus obtained exhibited excellent pearlescence and was evaluated as grade 5 in the appearance.

COMPARATIVE EXAMPLE

A uniform aqueous mixture, composed of 20 parts by weight of the PSE as the pearlescent agent and 80 parts by weight of a 75% by weight aqueous solution of a sodium α-olefinsulfonate having a number of carbon atoms of 14, was prepared by heating at 80° C. Almost all of the micelles in the mixtrue were found to be in the form of the lamellar micelles by the microscopic observation. This mixture was then cooled with agitation down to room temperature whereby crystals were formed to give an aqueous dispersion of the crystals.

The pearlescence of the aqueous dispersion thus obtained was very poor and the evaluation of the aqueous dispersion gave a grade 2 in the appearance.

What is claimed is:

1. A method for the preparation of an aqueous dispersion of pearlescent agent which comprises the steps of: (a) solubilizing 3 to 45% by weight, based on the resulting mixture, of an organic compound pearlescent agent having a melting point of 50 to 80° C. and capable of forming thin leaf crystals, in an aqueous solution of a surfactant at least a substantial portion of which forms the state of the middle phase ($M_1$ phase) liquid crystals, at a temperature higher than the melting point of the pearlescent agent to give a uniform aqueous mixture, and (b) cooling the uniform aqueous mixture to crystallize out the pearlescent agent in the mixture while the state of the middle phase ($M_1$ phase) liquid crystals of the surfactant is kept substantially unchanged.

2. The method as claimed in claim 1 wherein the solubilization of the pearlescent agent in the aqueous solution of the surfactant is effected at a temperature in the range from 50 to 95° C.

3. The method as claimed in claim 1 wherein the concentration of the surfactant in the aqueous solution is in the range from 35 to 65% by weight when the surfactant is a sodium α-olefin-sulfonate.

4. The method as claimed in claim 1 wherein the concentration of the surfactant in the aqueous solution is in the range from 30 to 50% by weight when the surfactant is a sodium polyoxyethylene lauryl ether sulfate.

5. The method as claimed in claim 1 wherein the concentration of the surfactant in the aqueous soltuion is in the range from 40 to 75% by weight when the surfactant is a long-chain alkyl quaternary ammonium chloride.

6. The method as claimed in claim 1 wherein the pearlescent agent is an ethyleneglycol di(fatty acid) ester.

7. A method for the preparation of an aqueous dispersion of a pearlescent agent which comprises the steps of: (a) solubilizing 3 to 80 parts by weight of an organic compound pearlescent agent having a melting point of 50 to 80° C. and capable of forming thin leaf crystals, in 100 parts by weight of an aqueous solution of an anionic surfactant at least a substantial portion of which forms the state of the middle phase ($M_1$ phase) liquid crystals, at a temperature higher than the melting point of the pearlescent agent to give a uniform aqueous mixture, and (b) cooling the uniform aqueous mixture to crystallize out the pearlescent agent in the mixture while the state of the middle phase ($M_1$ phase) liquid crystals of the surfactant is kept substantially unchanged.

8. A method for the preparation of an aqueous dispersion of pearlescent agent which comprises the steps of: (a) solubilizing 3 to 50 parts by weight of an organic compound pearlescent agent having a melting point of 50 to 80° C. and capable of forming thin leaf crystals, in 100 parts by weight of an aqueous solution of a cationic surfactant at least a substantial portion of which forms the state of the middle phase ($M_1$ phase) liquid crystals, at a temperature higher than the melting point of the pearlescent agent to give a uniform aqueous mixture, and (b) cooling the uniform aqueous mixture to crystallize out the pearlescent agent in the mixture while the state of the middle phase ($M_1$ phase) liquid crystals of the surfactant is kept substantially unchanged.

9. A method for the preparation of an aqueous dispersion of pearlescent agent which comprises the steps of: (a) solubilizing 3 to 60 parts by weight of an organic compound pearlescent agent having a melting point of 50 to 80° C. and capable of forming thin leaf crystals, in 100 parts by weight of an aqueous solution of an amphoteric or a nonionic surfactant at least a substantial portion of which forms the state of the middle phase ($M_1$ phase) liquid crystals, at a temperature higher than the melting point of the pearlescent agent to give a uniform aqueous mixture, and (b) cooling the uniform aqueous mixture to crystallize out the pearlescent agent in the mixture while the state of the middle phase ($M_1$ phase) liquid crystals of the surfactant is kept substantially unchanged.

* * * * *